United States Patent [19]
Dunn et al.

[11] Patent Number: 5,968,786
[45] Date of Patent: Oct. 19, 1999

[54] METHOD FOR PRODUCING LABELED SINGLE-STRANDED NUCLEIC ACID PROBES

[75] Inventors: John J. Dunn, Bellport; Mark A. Quesada, Middle Island; Matthew Randesi, Upton, all of N.Y.

[73] Assignee: Brookhaven Science Associates, Upton, N.Y.

[21] Appl. No.: 09/215,817

[22] Filed: Dec. 18, 1998

Related U.S. Application Data

[62] Division of application No. 08/966,958, Nov. 10, 1997.

[51] Int. Cl.$^6$ .................................................... C12P 19/34

[52] U.S. Cl. ........................................................ 435/91.53

[58] Field of Search ............................... 435/91.5, 91.53, 435/91.42

[56] References Cited

U.S. PATENT DOCUMENTS 5,354,656  10/1994  Sorge et al. ................................ 435/6

OTHER PUBLICATIONS

Chang et al, Gene, vol. 127: pp. 95–98, 1993.

Primary Examiner—Terry McKelvey
Attorney, Agent, or Firm—Margaret C. Bogosian

[57] ABSTRACT

Disclosed is a method for the introduction of unidirectional deletions in a cloned DNA segment. More specifically, the method comprises providing a recombinant DNA construct comprising a DNA segment of interest inserted in a cloning vector, the cloning vector having an f1 endonuclease recognition sequence adjacent to the insertion site of the DNA segment of interest. The recombinant DNA construct is then contacted with the protein pII encoded by gene II of phage f1 thereby generating a single-stranded nick. The nicked DNA is then contacted with *E. coli* Exonuclease III thereby expanding the single-stranded nick into a single-stranded gap. The single-stranded gapped DNA is then contacted with a single-strand-specific endonuclease thereby producing a linearized DNA molecule containing a double-stranded deletion corresponding in size to the single-stranded gap. The DNA treated in this manner is then incubated with DNA ligase under conditions appropriate for ligation. Also disclosed is a method for producing single-stranded DNA probes. In this embodiment, single-stranded gapped DNA, produced as described above, is contacted with a DNA polymerase in the presence of labeled nucleotides to fill in the gap. This DNA is then linearized by digestion with a restriction enzyme which cuts outside the DNA segment of interest. The product of this digestion is then denatured to produce a labeled single-stranded nucleic acid probe.

5 Claims, 1 Drawing Sheet

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 10754 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| GATCCTCTTC | TTCAGATGAA | GAAACAAGTA | AGGAAATGGA | AGTGAAACCC | AGTTCGGTGA | 60 |
| CTGCAGCCGC | AAGTCCTGTG | TACCAGGTAA | CCATGAAAAC | AGCTCAGTTT | TAAAGGGATG | 120 |
| TGCAGGGATT | GCCAGGACCT | TTCAGGTAGT | CCTACTTGGC | ATTGCCCAAG | GTTTCTGACT | 180 |
| TGAGATTCTG | GATAATAGTT | CTTGCCTTTC | CCCATGCTAA | GGGAAAGCTG | TTTCTCTGGC | 240 |
| ACGTAAATAG | GCATCCTGAG | TCATTTTATC | AAAGGTCAGC | TTCACTATAC | AATAACTAGG | 300 |
| ATAAATATAT | TTCAGAAAAA | TTGGCAAAAA | GTAGAAAATT | CATGATGGTA | AAACATTCCT | 360 |
| GATATTTTAA | AATCTCATTC | AAAAGTTACC | ACTTATTTTT | TGTAGTATGT | AACACTTTGT | 420 |
| TTTGTACCTT | TGGGTTTAAC | TTTCTATTCT | CTCCCGTTCC | ATGATTAAAG | AGAAACCTCT | 480 |
| CTAAATTTAT | TATATTATAA | TTAATATTTT | ACTCAAGCTG | AAACATTGTC | TCCCTTTTTG | 540 |
| CTTTACTAGT | TGAAAAGTCA | TATAGCTAGT | GTGCCTGCAC | TTACAGATCC | ATTCACTGAT | 600 |
| TTACTATTTA | TATCTACATA | CCAAAGAACA | TTTAATCGAC | TTTAAAAAAT | TGTTGACCAA | 660 |
| ACAGCATTCT | TCAACAGGAA | AGATATTTTA | AAGTCATAAC | AATTTAAAGA | GATTTTTGA | 720 |
| GTTGAGCCTT | ATTCTGTAAA | TGTACTTATT | ACTAATTTTT | AAAGGTTATC | TATTTTTACT | 780 |
| TACTTGCTTT | GATTAAATGT | GAAACATACC | AGGTTTGTGG | TAAGGTTGAG | CTGAAAATGA | 840 |
| AAATTTAGAC | TAATGAGTAA | GAAGCAGAAT | ATTGGAGCTT | TTAGTATGAT | AAACTAAACT | 900 |
| TTTAAATTCA | GCATACATTT | ACATAATGAA | CATTATTTCA | GTGTAACTTA | ATTTTTGGTT | 960 |
| TCTCATTTTT | TTCTCAGTTG | AATTATTCTT | CCTAGACTTT | AGGGGAAGAT | TATTTCTGAA | 1020 |
| GATTATCATA | ATTTAGGATT | CTATGTATAT | GTGTATGTAT | ATGTATATGT | ATATAACATG | 1080 |
| TACCTGGCTT | TATGAAACTT | CAAACAGTAC | AAGACAGTAT | AATAGTGAGA | AGTCCTCTTT | 1140 |
| CTCCCCAACC | ACCAGTCCCT | ATGCATTTCC | ACAGAGACAT | TCATTACCAG | GTTTTTTTTT | 1200 |
| CTTTTTTTTA | GTATCCTTCC | AGAGACATTC | CCTATATAAA | TAAGTAAACA | TAGTATTTGT | 1260 |
| ACTTCAGGAT | CATTTTTAAA | AACCTTGCCA | TAAATATTTG | AGGCATTTTT | TTTCTCTGTG | 1320 |
| TGATGGATTA | TATATTGCAA | ATTAGGTATA | TTGAATTTTC | TGGAATTCAT | CCAAATGTGT | 1380 |
| GGCAATTTTA | CCTCAGAATT | TTATTTGTTG | TTAAGCAAGA | ATGTAAGTCT | CAAATTAAAT | 1440 |
| TGATTGCTGC | TAATTTTTTA | CAAGCAAATT | AACCTTTAAT | TTTTAGGATT | TCTTTTAAAA | 1500 |
| TTAAATTGCA | TTTATTTTCC | CTCATGTTGA | AAGACTATTA | GGATAACAGA | AAGGTATGGA | 1560 |
| AATTGAGGTG | TCTCTTACGT | GCTTTTTAAG | GAAAACATTT | CTCCTTGGCC | TAATACTCAT | 1620 |
| TAGCAAAACA | TTTTATAATA | GAGAAACACT | ACTTGTGTGA | AAGCTAGTGC | AAATGGCCCA | 1680 |
| CTTTGATTTT | CTTCTTTCTA | GTATCTTGAA | TCTGGCATTG | CCACAAGCTT | TAAAAAAGTT | 1740 |
| TTATCAAATA | AGGACAACAA | AATTTCTAGC | TTGGAATTTT | TGTTCTCTAC | TGTTTTCTAA | 1800 |

-continued

```
AAGGTATCCC AAGAGAGGGG ATAAAGAATT ATTCATATCT TAAAAAACGA AGAAATGAAG    1860

ATTGTGTCAG TTCTCCTGAA ATAGATCTGT AGATCCAATT CAGTATCAAT GAACATCTTA    1920

AAAGGTTTTT TTCTGGAAAG TGACAAATTG ATTCAAAATT TTAAAAAGG AGGATCAGTT     1980

GGAGGGCTCA CACTAATTCA AAGCTATTAT ATATTCATCA AGACAGTGTG GTAATGGTTT    2040

AAAAACATAC AAATATATTG ATGGCACAGG ATAGAGAGTC CAGAAGTAGA CCCACATACA    2100

TACAGTTAGT CTTTTTTCTC CCTTTTAACA AAAGTGCCAA AGCAATTCAA TGGGGAAAGT    2160

CTTCAAGAAC TTGTGCTGAA ACAACTGGAT GATCTGTGTA GGAAAAAAAA CGAACCTAAC    2220

TTAGCTGACA CCATACACAA AAATATTGAT TTGAGATGGA TTGTGTACCT AGACATAAAA    2280

GATAAATCTC TGACGCTTTT AGAAGAAAAC ATAGGGAAAT ATAATCTTTA TTTTGTGACA    2340

GGCAAATATT TCCTCTAGAG GGTCACAAAA AGTAACTAAT AAGGGAAAAA AATTGACAAA    2400

CTGGACTTCA TCAAAATTAA TCATCTTTTT GTTCATCAAA GAAACCATTA AGAAAATGGG    2460

CAAACCATAG ACTAGGACAA AATATTCTCA TTACATATAT CTGTAAAGGA CTTATTTCCA    2520

GAATATACTT TTTTTAAAAT CGCTCACAAA TCACTAGTAA AAGGTAAATG ATTCAATGAA    2580

AAATAATGGG CATATCCTGC TGTAATCTCA AAAAAGGGC AGGAGGAGCA AAAGATGTGA     2640

ATAAACACTT TACAAAAGGA GTTATGTGAA TGGCCTCATT TATGATCAGA GGAATGCAGA    2700

TTAAATCCAT ATGAAACCTA GTTCTTCCAG AACTGCACAA TTTAAAAGCC TGACAGCATG    2760

AAATGTTAGC AAGGATGTGA AGCAGCTAGA TTCATAAACT TGCTAGTCAT GTAAAATAGT    2820

ACCACTACTT TGGAAAACTG GAACTTTTTA ACGTTAAATG TGTAACTCTT CTATTACTCA    2880

GCAGTTCCAC TCCTAAGTAT TAAATATTTA CCAAAAGAAA CGAAAATATG CCTATAAAGC    2940

CTTCTATTAG AATTAACTGT GCTGTTATTC ATTGCAGCAT TGTTTTGTTC GTTGTGTATC    3000

ATTGTTTTTT TAATAGTAAG AGACTGAAAA CAGCCTCAAT GTCCCATTAC TAGGAGACCA    3060

TTTAATTTAT AGTCATTGCT ATACTATCTA GCTGTAGAAA AATGAGAAGG ATCTTTATGT    3120

ATTGATATGT TTCTGAAATG TATTATTATG AAATGTAAAA AGCAGGATAC AATCCAGTAT    3180

ACATATATAT TTTTAAGTGT GTATAGATGT GGATAGAATA TCTCTAAAGG TATATTTAAA    3240

AAAATGTTTG GTGTCAGTTG CCCTTGAGAA GGGTTAAGAT AAAGAAGATA AAGGGTGAGA    3300

TAAAAAAAGA GGGACTTTCC ACAGTTTACC CTTTTGTACT TTTTGAATTT TCTATCATGA    3360

ATGCAATGCT ATACACAATA TAATTTTTTT AAAAAAATCC TATACTTAGA AATGCAGATT    3420

TGAGATCAGC AAAATCAGAA ATTTAAGAAG ATGTGGCATT CTAAGCAGAG AGGTCTAAAA    3480

CTGCTGATAA GAACACTTTG AATAATGTGA ACCTGACGTG CCCACCTGAT TTATGGGATA    3540

ATCTAAAACT ATTATTCCCA AATACTAAAC TGGCTACATC AGAATCACCT GGGGAGCTTT    3600

GTCAAAATAC CTGGCCTCTA GTTCTGAGAT TTTATTATTG TTCATTAGAC CAGTGCTAGG    3660

GCATGAATGT TTTGTGTTTA TCTTTTTTTT TTCTAACTTT TATTTTAGGT TTAGGGATAC    3720

ACATGAAGGT TTGTTCCATA GGTAAACATG TGTCACAGGG ATTTGTTGTA CATATTATTT    3780

CATCACCCAG GTGTGAAGCC CAGTACTCAA TAGTTATCTT TTCTGCTCCT TTTCCTTCTC    3840

CCACCCTCCC CTCTCAAATA GACTCCAATG TCTATTGTTT CCTTCTTTGT GTTCATAAGT    3900

TCTTATCATT ACCTCCCACT TATAAGTGAG AACATGCGGT AGTTGATTTT CTGTTTCTGC    3960

ATTAGTTTGC TAAGGATAAT GGCCTCCAGC TCCAATGTTT TGTATTTAAA AGCCTCCAAG    4020

TGACTCCTGG CTTAGCCAGC TGTGGAAACC ACTGGACTAA AACAAGCATG TCCTTACAAG    4080

CTTCCATTCG TTCCATGTTT TGGTCTTTTT TGGTTGAAGT TGTTTAGGAA GTACTGTGTT    4140

TGAGTTTATT CATTTCTTTA TGCATTCAGA AAACATTGGT CACCTGTTAT ACATTATACG    4200
```

| | |
|---|---|
| CCTATTACAC ATGAGGTTTT TAATGTATTT AGACCTGACA ATAGGAGTGT CACTTAGATG | 4260 |
| TGATCTCAGT GTTGTGGGTA ACTTTGTTTG TCTTTAATGA GAAATCTGGA ACATAGATGA | 4320 |
| TGATTTTTTC CTTTGAATTA ACTTAATGTG TTCTCTTCCC TACAGATTTC AGAACTTATA | 4380 |
| TTTCCACCTC TTCCAATGTG GCACCCTTTG CCCAGAAAAA AGCCAGGAAT GTATCGAGGG | 4440 |
| AATGGCCATC AGAATCACTA TCCTCCTCCT GTTCCATTTG GTTATCCAAA TCAGGGAAGA | 4500 |
| AAAAATAAAC CATATCGCCC AATTCCAGTG ACATGGGTAC CTCCTCCTGG AATGCATTGT | 4560 |
| GACCGGAATC ACTGGATTAA TCCTCACATG TTAGCACCTC ACTAACTTCG TTTTTGATTG | 4620 |
| TGTTGGTGTC ATGTTGAGAA AAAGGTAGAA TAAACCTTAC TACACATTAA AAGTTAAAAG | 4680 |
| TTCTTACTAA TAGTAGTGAA GTTAGATGGG CCAAACCATC AAACTTATTT TTATAGAAGT | 4740 |
| TATTGAGAAT AATCTTTCTT AAAAAATATA TGCACTTTAG ATATTGATAT AGTTTGAGAA | 4800 |
| ATTTTATTAA AGTTAGTCAA GTGCCTAAGT TTTTAATATT GGACTTGAGT ATTTATATAT | 4860 |
| TGTGCATCAA CTCTGTTGGA TACGAGAACA CTGTAGAAGT GGACGATTTG TTCTAGCACC | 4920 |
| TTTGAGAATT TACTTTATGG AGCGTATGTA AGTTATTTAT ATACAAGGAA ATCTATTTTA | 4980 |
| TGTCGTTGTT TAAGAGAATT GTGTGAAATC ATGTAGTTGC AAATAAAAAA TAGTTTGAGG | 5040 |
| CATGACAACG CGTGTTTCTG TTGTGTGCAT AAAAGGGGAA AAGAACGGGT ATTTCCCTTC | 5100 |
| AATGTATTTA ACTAAATAGC AAAAACATTA AACAGAACGT AAGAATTTTA AAATTTCCTT | 5160 |
| TGAAAAATCA ACTATTAACC ATACTTTTCC TAAAAGACCA CATATCAGAA TATGCATATG | 5220 |
| AAAAGTTAAA AATTTGTTAG TGGTAGTTAT TGAAAATATA ATAAAACATC TTTTAACTAT | 5280 |
| CAGTGTCACT ATACATAGGG TTTTTTAACA AAGAATTTGG CTCGTACTAA TTTTGACATG | 5340 |
| ACATCTGACT TACATGTCTA ATGCCATTGC ATAAAGTAGA TGTGTTCTTA CAGCTGCTCT | 5400 |
| AATCTCTGTC CTTGTGCTTT TTTTAAAAAC ATTTAAGTCT TTACTAGAGG CCTAAAATAA | 5460 |
| AGTCAAATAA TACAATACTT CAGATTCTTC AGTAGTCCAT ATTTATACAA CTGTAATTCC | 5520 |
| ATCATCTTGT AAGGGTACTT GAACTACAAA AGAAAAAAA GAGATATCTC TATAAGAGTT | 5580 |
| TTGATTTTTC TCCAAAGGTA AATTTTTAAA AACTAAGATC AGCAATACTT TTTCCATCAC | 5640 |
| CTTCATCTTT AAATTTGCAG TCTTAAATTA TTTGACTTAC CAGAAAAATC ACAACTTGCT | 5700 |
| AATAAATCAT TGAATGCCAT GGCTATTCCA CAAATTATTG TTATTTTTAG GAAGATAAAT | 5760 |
| TCTGTTGAAA TACAAAACTG CACAAATCAT AAAGGTATAG CTCAATAGTA TGAAAATGTC | 5820 |
| AGTTTTTAAA GTTTGCAACT TCAGAAAACT CATTTTTAAA CCTTAGAGAC TTTTCTAGCT | 5880 |
| TTAATATTGT ACTCTTTAAG CCATACACAA TTTTAACATC TCTCTAAACC ATATCTACTC | 5940 |
| TTTTCCTGAA ATCTAGTGAC TGCCTATTCA AACATGAGCA TGTTTGTTTA TTAGTGTCAA | 6000 |
| AAGGGAGATG CGTTTTATCA ATTTTTTTTA ACCAAAGTTA TTGAAAGAAA AAAAGGAAAA | 6060 |
| AAAAATTACT TTCAGAGTCA TCACACTGCT TCCTTATGGG TCCTTGAGAG TTTTGTGGTG | 6120 |
| ATAATGACAG ATTTGTAGGT GATTGGCGTA AAGTTGGAAA GTTTCAAGTA TTTTTATCAT | 6180 |
| GAAGTTAGCA GACAGAATTT ATTTATTGCT TTGCTTATGA GCAAATTGGT CCTCATCTGT | 6240 |
| AGGTTTTTCA TCTGTATTTA ACCATGTATG GAAAATACTC AAAAATTAAA AAAATACAAA | 6300 |
| TTTTAAAATA TAACTACATT GCATTAGGTA TTATCTAGAT TTAAAGGATG TACATAGGTT | 6360 |
| ATATGCAAAT ACGAAGCCAT TTTATATAAG GCACTTGAGC ATCTGAGATT TTGGTATCCA | 6420 |
| GGAGGTCCTG GAACAAATCC TCCAAGGATA CTGAGGGATG ACTATATAGG TTTGTTGGGA | 6480 |
| AAATCAGAAG CATAATAGTG TAAAGAAGGA AGTGTTATTT TTGGCACATA CTTAGTAGCC | 6540 |
| AGAACATTCC ACGTTACTAC AAAATCTCCT TAATTAGTTT GACGATTAAA TGACAGGGCC | 6600 |

```
TCTTGGGGAA ACCACTAGTT TTGATTCAAC TGCATACAGG TAGATGTTAT TACTCATAGA    6660

AGATTCTGCC AGTGTTTCGA CTACCCATCC TCCACCTTGT CCTGAAACTT ATTTAGAGCA    6720

AAAGAAAGCT CTCATAAATA TGGCTTTTCC AATCTATTCC TAATGAAATA AAACTGTCAC    6780

TCAGCAACTG GGTCTTAAGT TCTAGCAAGC ATGGGGTACA AAAGTTTGCC AAACCCTTTT    6840

TTAGTAGTAA TTATGACTCT AGGTGCTTTG TTCTCTTAAG TTTGTCTCCC TTAGACAACT    6900

CCAAGGTGGT CTTAAAACAT GACTACATAA TTTCAGCTTG AAAGCCTTAT CGGGCTATTT    6960

CAAGCAGGAG TGGTTTATCA CTGAACAATA ATTTGTTTAA ATTCTCCATT TTATTTTTGT    7020

ATTTGTAGGC ATAACTGCAA AGCTCTAAAT TTTATAGGTT AAACTTGGAT ATTTGAAAAA    7080

AAAAGTTTTA GTAAGTTCTA TCACATTAAT ACTAAAGCAG TGCTTATTTC TGGTTTATTA    7140

GTATAATATT TATCTCAAAG TATTTAACTT TTTAGTAAAC TTCTGTGGTT CCAAGTTAAG    7200

ATAATAAAGC ATTTATGTTG ACTTCTCACT AACAGAGGTA TGTGTTAATT TCTTATTTTA    7260

TGATTAGGAA GAGGGAAAAA TACAACACCT ACCATGTACA GTTTATTGTG TAGCCATTCT    7320

GTCCATTTTA CAGATAATAG TAAATAATTT TTTTAATTTT TATTACTACA TGGCAACAAC    7380

TTATTTAATC ATCACAGCCT CAGGGGGTAT GTACCATTAT CATCCCAGTT AGATAAGGAT    7440

TCCAGAGAAG TTAAAAATGC CCAAGATCAC AGAAAACTAA ATAATGAAGC TCTGACTTAA    7500

AACCCAGCTG GGCTTTTTTA AGGCCCATGC CATGGTACCT TGCCATCAGA TTCATTTTGT    7560

TACCTATAAA ATCTACCAAA TCTTGAAACT TGTAAGAAGG TTCATTATCA GACCAAGATT    7620

TTTTTAAAAA AAGGAACCAT GCGAAGGTAA ATTAATGAGA ATATAAGACA TTAAAGTATC    7680

TATTGATTAA CCACTAATAA ATCTTTGGCC AAGTTTCTTG TTACAAACTA CTCAATATAT    7740

CTGAAGAGGG AGCTGGCTGA TCATCTGATA GTAATTTTAT TGCTGGAAAT AGAAATTAAA    7800

TTGCAATAAA CAGTACAACC CAGTAGAGTG AAGACTGAGA TGACAAAGCA AACTGTACCA    7860

ATGACTTGTT ACATGGAAAG ATCACACATA ATGAGTAGTA ATTCCCAAGT CTGTCACAGT    7920

CTTTAACTTT TTTTTCTTAC TTATCAGTTA CTTGGCAATT TAACAGAGTG TACAACGTTA    7980

GTAAACTTTG TGCCAAATTT CTTCATATAC TCTGGAATCT ATTGCAATGG ATGAAGCAAT    8040

AACATTGTGA GGCTCTTACG GAAACACAAC AATATCCCTG CATTGCATAT GGCACTTTAT    8100

GGCATTGACT CGTACTGCGA AGTTGTCACA CAAGCACTCA TGAGCACAAG GAAGGCTCA     8160

TGCAATTCCT CTTTAAAATA TGTACATTTT ATTCATTGCA GAAACCATCA CCCACTTCCA    8220

AATTTAATAG CATTAGTCCA TCTTCTATGT TCCTTTGTTC TTTCATGTAT ACTTTTAAGG    8280

GTAACATAAG GACAAAAGTG GAAGCATGTT TAACCCTTAT CAAAAACAAA TTCACCATTA    8340

AGACTTGTAG CAGATACATC ACTGCAATTA GGGTAGTTTG ATGTTTATTC TGTAAAGCAC    8400

ACAATCAGCA CAAATAAAAG TACTGAATTT GTTTCTCCTA TCAAAAAAAA AAAAAATACC    8460

TAGCTACAAA AATTTCTTCC ATAAAAGTTA AGAAACATAA TCATGGGAGA CTTTGTGTTT    8520

AAATTTCATA GGACTTAAAA ATACTAATTA TGATTTAGAC AGCAATGCCA TGGCTAAAAA    8580

ATGTTTATTT GTGTGTATAC ATATATAAAA TTTATAAAAT ATAAATCCAT AGGGAATATG    8640

GGTGAAACAC ATTTCTATCT AGACTAGAGG TTTAATGGAT CATTTCTGTG TATAATATTA    8700

GTGTTATGAC CAATAAATAT ATGAACACTA ATACAAATT AAAACATTTA TTTTGGGAAT     8760

CAAAATTAAT AATGCCCAAT ATTGGTGAGG GTGTAGGGGA AGCAGTCTCT TACAGTGTTA    8820

CTAGAGGCTT AAAGAGGAGG GCAGTTACAC CTTCTTGAAG TATATATCCC TTGATCAAGC    8880

AATTGTACGT ACTTCTAGAA ATTTATCTAC AGAAGTACTC AAACGAGGAC CATTACCTAC    8940

GTAATAAGTG TTCACTGCAA AATTGTTTTG GGTGGCAAAA ATAACAAAAG CCCAAGTAGC    9000
```

```
CACCAATAGA TGAACAGTTT AATAAAATTT GAACATCTGT TCAAGGAAAT GCTGTGGAAA    9060

ATACCATGTA GCCATTAAAA AAGAGTAGAA TAAAAAAAAA AATGGTATGC CTAGAATGGT    9120

GCTAGTATTG TCTGGGGGCA AAAAATTGTT AATGGTAGTT AGTGTTCTCA AGGCGGGGAA    9180

TGGGACAAAT ACAGAGAATA TTATTTTTCT ACTTTCAACA TTTTGATCTT TAAATTTTTA    9240

TATTGAGCAT TATTACTTTG TAACTGGAGG GTAAAAAGAC ACTTTCTCAA AGGGCTTTAA    9300

GACAAGTTCA ATGGATTTAT TTTTAGCAGA TGCAAATGCT GCCATCAGTG ATAATCAAAT    9360

TGTATGTTTT GTGGACAATC TGTTGTATTT CTGAATTAAA CAATTGCAAT GTGGCTACAG    9420

TTTTATGTTT GTAATCATAC TGTGTCTACA AGGAAATATT CTGAAATAGT AAATACTTAT    9480

AATGGGGTAG CAATAGTGCA TAGTTTCCTC CAGTGTTCCC ATTATATATA ATATGATAAT    9540

ATTCATGAGA AAAATGTTAA ATATAGTATT TGGTGGGAGA AAACCCCATT ATTAAGAAAA    9600

AGTATTTAGG GAGTAGAGGG ATGCAAAAAA GAAAAGTGAA AGAAAATTTA TTAAATACCT    9660

TGGAAATAAA CTTTAACAAC AACAAAAAAG GAGTGAGTCC TATAGAGAAG AAAATTATTA    9720

AAATTTGGTG AAAGACAAAA CTGAATAGAA GAATATATCA TTTTTAAATG GACCTGATAT    9780

TATAAAAGCT TTACTTTTCT ACAAATTAAT ACATAAAGTC AATAGAAATC ATAATTTTAA    9840

AATCCCAGCA AAATTTTATG TAACTAGAAA GCCTGATTTT AAGTTTACAT GGAAGAGTAA    9900

ATTTCAAGAA TTACCAAGAA TTGTTTTAAG TAAAACAATG AGCAGAGAGT ATTTTTCCTT    9960

TTACATTATT TATTAATACA TACTTGAAGT ATAACATAGG AATAAACTAA TTCACCAGTG   10020

AAACAGAATT ACAGATCCAG AACCGAAACA TTTATATACA GAAGTTTGGT GAATGGGGCT   10080

TTTCAAATTA AAGATGAAGA ATCCACTAAT CAAAAATTAA TAGGTATTCT TATACACCAA   10140

TAACAGACAA ACAGAGAGCC AAATCATGAG TGAACTCCCA TTCACAATTG CTTCAAAGAG   10200

AATAAAATAC CTACGAATCC AACCTACAAG GGATGTGAAG GACCTCTTCA AGGAGAACTA   10260

CAAACCACTG CTCAATGAAA TAAAAGAGGA TACAAACAAA CGGAAGAACA TTCCATGCTC   10320

ATGGGTAGGA AGAATCAATA TCGTGAAAAT GGCCATACTG CCCAAGGCAA TTTATAGATT   10380

CAATGCCATC CCCATCAAGC TACCAATGAC TTTCTTCACA GAATTGGAAA AAACTACTTT   10440

AAAGTTCATA TGGAACCAAA AAAGAGCCCG CATTGCCAAC TCAATCCTAA GCCAAAAGAA   10500

CAAAGCTGGA GGCATCACAC TACCTGACTT CAAACTACAC TACAAGCCTA CAGTAACCAA   10560

AACAGCATGG TATTGGTGCC AAAACAGAGA TATAAACCAA TCGAACAGAA CAGAGCCCTC   10620

AGAAATAACG CCACATATCT ACAACTATCT GATCTTTGAC AAACCTGAGA AAACAAGCA    10680

ATGGGGAAAG GATTCCCTAT TTAATAAATG GTGCTGGGAA AACTGGCTAG CCATATATAG   10740

AAAGCTGAAA CTGG                                                    10754
```

METHOD FOR PRODUCING LABELED SINGLE-STRANDED NUCLEIC ACID PROBES

This is a divisional of copending application Ser. No. 08/966,958 filed Nov. 10, 1997.

This invention was made with Government support under contract number DE-AC02-76CH00016, awarded by the U.S. Department of Energy. The Government has certain rights in the invention.

BACKGROUND OF THE INVENTION

DNA sequencing is a fundamental research tool with wide-ranging applications. A common approach to DNA sequencing involves the subcloning of a large DNA fragments as smaller, overlapping fragments, the sequences of which are subsequently determined using the dideoxynucleotide chain termination approach (Sanger and Coulson, Proc. Natl. Acad. Sci. USA 74: 5463 (1977)).

Subcloning, and the restriction mapping required to efficiently subclone fragments, is a time consuming and labor intensive process. However, given the limitations associated with the amount of sequence which can be determined from a single extension reaction, it is necessary to initiate new sequencing reactions at a distance of about every 300–400 base pairs along a fragment, the sequence of which is to be determined.

One alternative to the subcloning approach is described by Henikoff et al. in U.S. Pat. Nos. 4,843,003 and 4,889,799. More specifically, Henikoff et al. describe a method in which a vector containing a DNA sequence of interest is linearized by digestion at two restriction endonuclease recognition sites, one generating a 5' overhang and the other a blunt end or 3' overhang. Timed digestion with E. coli Exo III from the 5' overhang, followed by treatment with a single-strand-specific nuclease generates a nested array of deletions. Unfortunately, this technique also is limited by the need for conveniently located restriction endonuclease recognition sequences.

An alternative to the approach described above was outlined by Chang et al. (Gene 127: 95 (1993)). Chang et al. describe a method in which a single-stranded nick is introduced at a position adjacent to the site at which a DNA fragment having a sequence which is to be determined is inserted in a cloning vector. The nick in the DNA is then extended under controlled digestion conditions to produce a single-stranded gap. The single-stranded gap is then treated with a nuclease which specifically digests single-stranded DNA, thereby producing a deletion within the DNA sequence of interest.

Chang et al. specifically report that the single-stranded nick in the DNA of interest cannot be expanded by treatment with E. coli Exo III. Given the fact that Exo III is a well-understood, relatively inexpensive enzyme, Chang et al. note that this is an unfortunate finding (page 96, column 2). The development of protocols which would enable the use of Exo III in such a DNA sequencing strategy would represent an important improvement in the art.

SUMMARY OF THE INVENTION

The present invention relates, in one embodiment, to a method for the introduction of unidirectional deletions in a cloned DNA segment. More specifically, the method comprises providing a recombinant DNA construct comprising a DNA segment of interest inserted in a cloning vector, the cloning vector having an f1 endonuclease recognition sequence adjacent to the insertion site of the DNA segment of interest. The recombinant DNA construct is then contacted with the protein pII encoded by gene II of phage f1 thereby generating a single-stranded nick. The nicked DNA is then contacted with E. coli Exonuclease III thereby expanding the single-stranded nick into a single-stranded gap. The single-stranded gapped DNA is then contacted with a single-strand-specific endonuclease thereby producing a linearized DNA molecule containing a double-stranded deletion corresponding in size to the single-stranded gap. The DNA treated in this manner is then incubated with DNA ligase under conditions appropriate for ligation.

In another embodiment, the invention relates to methods for producing single-stranded DNA probes. In this embodiment, single-stranded gapped DNA, produced as described above, is contacted with a DNA polymerase in the presence of labeled nucleotides to fill in the gap. This DNA is then linearized by digestion with a restriction enzyme which cuts outside the DNA segment of interest. The product of this digestion is then denatured to produce a labeled single-stranded nucleic acid probe.

DETAILED DESCRIPTION OF THE INVENTION

Figure 1:
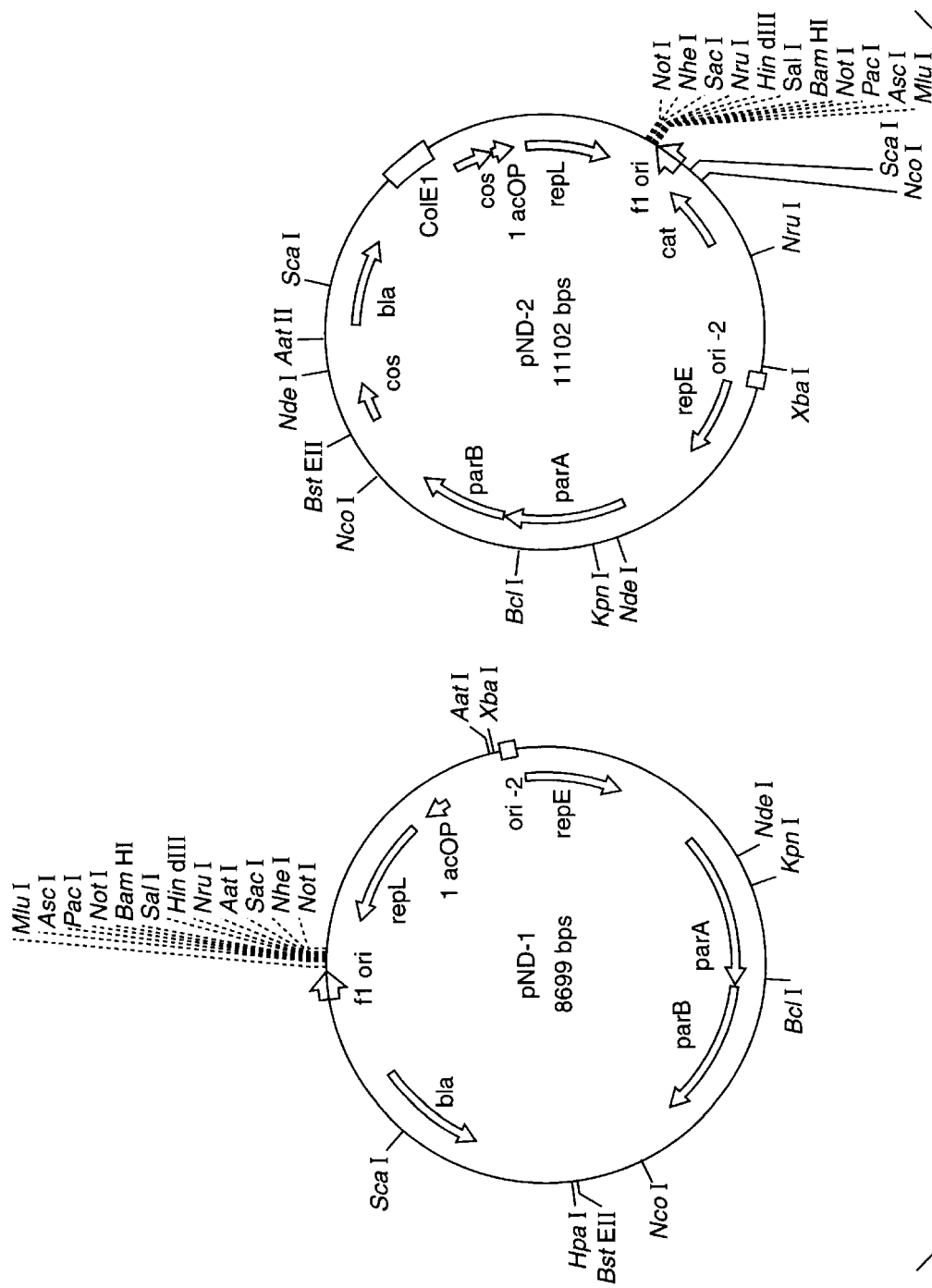
FIG. 1 is a diagrammatic representation of the vectors pND-1 and pND-2.

The subject invention relates to a universal method for generating a nested set of unidirectional deletions within a cloned DNA fragment. The method is applicable to a variety of molecular biological applications including, for example, DNA sequencing and the production of labeled single-stranded probe sequences. The method is based on the surprising discovery that E. coli Exo III is capable of extending a single-stranded nick, introduced into double-stranded DNA by the phage f1, gene II product, into a gapped structure.

As discussed in the background section, the prior art teaches that E. coli Exo III is incapable of extending a nick in double-stranded DNA, introduced into double-stranded DNA by the phage f1, gene II product, into a gapped structure. As shown in the experiments described below, this teaching is incorrect.

More specifically, Applicants produced a recombinant DNA construct comprising a DNA segment of interest inserted in a cloning vector, the cloning vector having an f1 endonuclease recognition sequence adjacent the insertion site of the DNA segment of interest. The recombinant DNA construct was contacted with the protein pII encoded by gene II of phage f1 thereby generating a single-stranded nick. This digestion was carried out in the presence of the divalent cation $Mn^{2+}$. The nicked DNA was then treated with E. coli Exo III thereby expanding the single-stranded nick into a single-stranded gapped structure. The Exo III digestions were carried out under timed conditions to generate molecules having singled-stranded gaps of varying sizes.

The single-stranded gapped DNA is then treated with a single-strand-specific endonuclease (e.g., mung bean or S1 endonuclease) thereby producing a linearized DNA molecule containing a double-stranded deletion corresponding in size to the single-stranded gap. The DNA containing the double stranded deletion is then incubated with DNA ligase under conditions appropriate for ligation. In a preferred embodiment of the present invention, dNTPs and DNA polymerase are included in the ligation reaction to blunt any ragged ends which may have been produced in the deletion process.

When used in connection with DNA sequencing protocols, this method of producing unidirectional nested deletions can be fine-tuned to result in an ordered set of nested deletions whose ends are separated by about 300–400 base pairs. This allows rapid sequencing across one strand of a cloned DNA fragment using a universal primer. Any gaps remaining after this process can be closed by primer walking on the original clone. Even highly repeated DNA can easily be assembled correctly, knowing the relative locations of the sequences obtained. As shown in the Exemplification section which follows, the disclosed method has been employed to determine the DNA sequence of cloned fragments at least as large as 17 kb. It is reasonable to postulate an upper limit of 40–50 kb for the size of cloned fragments which can be sequenced in this manner.

Two specific vectors (pND-1 and pND-2) were used in connection with the experiments described below. Both are single-copy amplifiable vectors stably maintained at low copy number by the F replication and partitioning functions and can be amplified from an IPTG-inducible P1 lytic replicon to prepare DNA. A synthetic version of the phage f1 origin of replication is located a short distance upstream of the multiple cloning site. Vector pND-1 was used primarily for obtaining clones by transformation or electroporation. Vector pND-2 has phage lambda cos sites that allow efficient cloning of 30–40 kbp fragments in a lambda packaging system.

Although the demonstration below was accomplished with the two low copy number vectors, one of skill in the art will recognize that the teachings of the present invention apply to any type of cloning vector.

Reaction conditions have been defined where purified f1 gene 2 protein efficiently introduces a strand-specific single nick in the f1 origin sequence with very little rejoining. Large amounts of stable gene 2 protein are obtained using recombinant DNA production techniques. The Exo III digestion is highly synchronous and processive, and the deletion lengths are proportional to incubation time. In one embodiment, to prevent undeleted DNA from giving rise to clones, treated DNA is digested with one of several restriction enzymes whose 8-base recognition sequences lie between the f1 origin and the cloning site. Nested deletion clones are then obtained by electroporation.

Pooling samples from several different times of Exo III digestion before subsequent treatment generates a good distribution of deletion clones. Growth and amplification of randomly selected clones in 1 ml of medium in 96-well format followed by a simple DNA preparation protocol provides ample DNA for analyzing deletion length by gel electrophoresis and for DNA sequencing reactions. Imaging and sizing software is now being tested for automated selection of an appropriate set of deletions for sequencing.

In addition to the method for producing nested deletions discussed above, the invention also relates to a method for producing labeled single-stranded DNA probes. The method for producing labeled single-stranded DNA probes is essentially identical to the method described above for producing nested deletions, through the DNA gapping step. However, rather than digesting single-stranded DNA with an endonuclease following the gapping step, the gap is instead filled in by a DNA polymerase in the presence of labeled dNTPs. The molecule is then linearizing by digestion with a restriction enzyme which cuts outside the DNA segment of interest. The product is then denatured (e.g., by heating) to produce a labeled single-stranded nucleic acid probe.

EXEMPLIFICATION

Materials

The following reaction buffers were prepared:

i) 10× GeneII buffer 200 mM Tris pH 8.0 800 mM KCl 50 mM DTT ii) 1× ExoIII Buffer(USB) 66 mM TrisCl pH 8.0 6.6 mM $MgCl_2$ 5 mM DTT 50 μg/ml BSA iii) S1 Stop Mix 0.3M TrisCl 50 mM EDTA iv) 2× Fill-in & Ligation Mix 40 mM Tris pH 7.6 20 mM $MgCl_2$ 20 mM DTT 1.2 mM ATP 200 μM of each dNTP Methods Double-stranded DNA was nicked by combining the following reagents:

2 μg DNA(for inserts >20 kb: 4 μg DNA) 4 μl 10× Gene II Buffer 2 μl 50 mM $MnCl_2$ 20 μl GeneII serially diluted 1/8

The total reaction volume was brought to 40 μl with the addition of sterile water and the mixture was incubated at 37° C. for 1 hour. The nicked DNA was then phenol extracted and ethanol precipitated. The nicked DNA was then resuspended in 50 μl 1× Exo III Buffer (USB).

2 μl Exo III (200 U, USB) was added to a prewarmed tube containing phenol extracted, nicked DNA. The mixture was incubated at 370° C. 2.5 μl aliquots were sampled at 30 second intervals and mixed with 2.5 μl of S1 nuclease mix (0.5 μl S1 nuclease buffer, 1.25 U S1 nuclease, brought to 2.5 μl with distilled water) on ice. After last time point, all tubes were transferred to 30° C. for 30 minutes. 1 μl of S1 nuclease stop mix was added and the tubes were heated at 70° C. for 10 minutes. 2 μl of each time point was checked by gel electrophoresis. All time points were then combined and ethanol precipitated. The DNA was resuspended in 25 μl TesI.

To recircularize the deletion-containing DNAs, 25 μl 2× fill-in and ligation mix was added to the above, together with 1 μl T4 DNA ligase (6 Weiss units) and 0.5 μl (2 units) T4 DNA polymerase. The mixture was sonicated at 14 degree C for 10 minutes and incubated at 14° C. overnight. The enzymes were heat-inactivated at 68° C. for 15 minutes, followed by digestion with a restriction enzyme having an uncommon recognition sequence (e.g., PacI or AscI). Following digestion, the DNA was phenol extracted, ethanol precipitated and resuspended in 10 μl sterile water. Cells were then transformed by electroporation with 5 μl DNA and plated on selected antibiotics.

Results

A partial sequence of the human adenovirus receptor gene was determined in the manner described above. A BAC clone containing the human adenovirus receptor gene was purchased from Research Genetics (Huntsville, Ala.). The human DNA insert in this BAC clone is approximately 110 kilobases in length. The BAC DNA was isolated for subcloning by standard techniques. The DNA was digested with the restriction enzyme Bam H1 which yielded approximately 16 fragments. These fragments were individually subcloned into the pND2 vector. All subclones were sequenced in both directions. Nested deletions were performed on 5 of these fragments. In particular, a 10 kb fragment was sequenced completely by the nested deletion strategy. The sequence determined is shown in SEQ ID NO: 1.

We claim:

1. A method for producing a labeled single-stranded nucleic acid probe, comprising:

a) contacting a recombinant DNA construct comprising a DNA of interest inserted in a cloning vector, the cloning vector having an f1 endonuclease recognition sequence adjacent to an insertion site of the DNA of interest, with protein pII encoded by gene II of phage f1 thereby generating a recombinant DNA construct with a single-stranded nick;

b) digesting the single-strand nicked recombinant DNA construct of step a) with E. coli exonuclease III thereby expanding the single-stranded nick into a single-stranded gap, thereby generating a recombinant DNA construct with a single-stranded gap;

c) contacting the single-stranded gapped DNA construct of step b) with a DNA polymerase in the presence of labeled nucleotides, thereby labeling the 3' end of the gapped strand of the single-stranded gapped DNA construct;

d) linearizing the labeled single-stranded gapped DNA construct of step c) by digestion with a restriction enzyme which cuts outside the DNA of interest; and e) denaturing the linearized labeled single-stranded gapped DNA construct produced by step d) to produce the labeled single-stranded nucleic acid probe.

2. The method of claim 1 wherein the cloning vector is a single copy cloning vector.

3. The method of claim 1 wherein the cloning vector is a high copy cloning vector.

4. The method of claim 1 wherein the exonuclease III digestion of step b) is timed to produce a single-stranded gap having a specific length, the time of digestion required for said specific length being determined by empirical experimentation.

5. The method of claim 1 wherein step a) is carried out in a buffer containing the divalent cation $Mn^{2+}$.

* * * * *